(12) United States Patent
Willbold

(10) Patent No.: US 9,591,845 B2
(45) Date of Patent: Mar. 14, 2017

(54) METHOD FOR TREATING BLOOD, BLOOD PRODUCTS AND ORGANS

(71) Applicant: FORSCHUNGSZENTRUM JUELICH GMBH, Juelich (DE)

(72) Inventor: Dieter Willbold, Juelich (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 14/388,865

(22) PCT Filed: Apr. 5, 2013

(86) PCT No.: PCT/EP2013/057160
§ 371 (c)(1),
(2) Date: Sep. 29, 2014

(87) PCT Pub. No.: WO2013/150126
PCT Pub. Date: Oct. 10, 2013

(65) Prior Publication Data
US 2015/0282477 A1 Oct. 8, 2015

(30) Foreign Application Priority Data

Apr. 5, 2012 (DE) .......... 10 2012 102 999
Sep. 14, 2012 (DE) .......... 10 2012 108 598
Sep. 14, 2012 (DE) .......... 10 2012 108 599

(51) Int. Cl.
A61K 38/00 (2006.01)
A01N 1/02 (2006.01)
C07K 7/06 (2006.01)
C07K 7/08 (2006.01)
C07K 14/47 (2006.01)

(52) U.S. Cl.
CPC .............. *A01N 1/0226* (2013.01); *C07K 7/06* (2013.01); *C07K 7/08* (2013.01); *C07K 14/4711* (2013.01); *A61K 38/00* (2013.01); *G01N 2333/4709* (2013.01)

(58) Field of Classification Search
None
See application file for complete search history.

(56) References Cited

U.S. PATENT DOCUMENTS

| 5,854,204 A | 12/1998 | Findeis et al. |
| 5,968,820 A | 10/1999 | Zborowski et al. |
| 6,306,821 B1 | 10/2001 | Mikos et al. |
| 6,319,498 B1 | 11/2001 | Findeis et al. |
| 6,384,105 B1 | 5/2002 | He et al. |
| 6,423,790 B1 | 7/2002 | He et al. |
| 6,759,485 B2 | 7/2004 | He et al. |
| 7,658,917 B2 | 2/2010 | Findeis et al. |
| 7,951,796 B2 | 5/2011 | Korth et al. |
| 8,318,175 B2 | 11/2012 | Frangione et al. |
| 8,445,438 B2 | 5/2013 | Sundaram et al. |
| 9,051,364 B2 | 6/2015 | Willbold et al. |
| 2002/0022676 A1 | 2/2002 | He et al. |
| 2002/0098173 A1 | 7/2002 | Findeis et al. |
| 2002/0133001 A1 | 9/2002 | Gefter et al. |
| 2002/0177668 A1 | 11/2002 | He et al. |
| 2004/0005307 A1 | 1/2004 | Findeis et al. |
| 2004/0143093 A1 | 7/2004 | Zahn et al. |
| 2005/0158306 A1 | 7/2005 | Halikas |
| 2007/0010435 A1 | 1/2007 | Frangione et al. |
| 2007/0092508 A1 | 4/2007 | Stein et al. |
| 2008/0051690 A1 | 2/2008 | Mattner et al. |
| 2009/0042211 A1 | 2/2009 | Birkmann et al. |
| 2009/0124001 A1 | 5/2009 | Korth et al. |
| 2009/0175853 A1 | 7/2009 | Frangione et al. |
| 2010/0166695 A1 | 7/2010 | Bundle et al. |
| 2011/0009343 A1 | 1/2011 | Findeies et al. |
| 2011/0189290 A1* | 8/2011 | Sundaram et al. ........... 424/484 |
| 2011/0201987 A1 | 8/2011 | Mattner et al. |
| 2011/0243949 A1 | 10/2011 | Willbold et al. |
| 2012/0226258 A1 | 9/2012 | Otto et al. |
| 2013/0045216 A1 | 2/2013 | Frangione et al. |
| 2013/0143822 A1 | 6/2013 | Funke et al. |

FOREIGN PATENT DOCUMENTS

| CN | 1665838 A | 9/2005 |
| CN | 101538329 A | 9/2009 |
| CN | 102224168 A | 10/2011 |
| CN | 102233128 A | 11/2011 |
| DE | 10117281 A1 | 10/2002 |
| DE | 69621607 A1 | 1/2003 |
| DE | 102005009909 A1 | 9/2006 |
| DE | 60026983 T2 | 1/2007 |
| DE | 102005031429 A1 | 1/2007 |
| DE | 102005063175 A1 | 2/2007 |
| DE | 102006015140 A1 | 10/2007 |

(Continued)

OTHER PUBLICATIONS

Hermann et al, Device for continuous extracorporeal blood purification using target-specific metal nanomagnets, Nephrol Dial Transplant (2011) 26: 2948-2954.*
Lewczuk et al, Amyloid β peptides in plasma in early diagnosis of Alzheimer's disease: A multicenter study with multiplexing, Experimental Neurology 223 (2010) 366-370.*
Focus online "Koennen Bluttransfusionen Alzheimer uebertragen?", Feb. 12, 2012.
Zhang Guobao et al: "Multiple-peptide conjugates for binding beta-amyloid plaques of Alzheimer's disease", Bioconjugate Chemistry, ACS, Washington, DC, US, vol. 14, No. 1, Jan. 1, 2003 (Jan. 1, 2003), pp. 86-92.
Katja Wiesehan et al: "Selection of D-Amino-Acid Peptides That Bind to Alzheimer's Disease Amyloid Peptide A [beta]142 by Mirror Image Phage Display", Chembiochem, vol. 4, No. 8, Aug. 4, 2003 (Aug. 4, 2003), pp. 748-753.
Sidhartha M. Chafekar et al: "Branched KLVFF Tetramers Strongly Potentiate Inhibition of [beta]-Amyloid Aggregation", Chembiochem, vol. 8, No. 15, Oct. 15, 2007 (Oct. 15, 2007), pp. 1857-1864.

(Continued)

Primary Examiner — James H Alstrum Acevedo
Assistant Examiner — Sergio Coffa
(74) Attorney, Agent, or Firm — Abel Law Group, LLP

(57) ABSTRACT

The invention relates to the treatment of blood, blood products and organs for the removal and/or detoxification of amyloid-beta oligomers.

15 Claims, 4 Drawing Sheets

(56) References Cited

FOREIGN PATENT DOCUMENTS

| | | | |
|---|---|---|---|
| DE | 102008037564 A1 | 5/2010 | |
| DE | 102009037015 A1 | 2/2011 | |
| DE | 102010019336 A1 | 11/2011 | |
| DE | 102010017130 A1 | 12/2011 | |
| WO | 0242462 A2 | 5/2002 | |
| WO | 02081505 A2 | 10/2002 | |
| WO | 2004056318 A2 | 7/2004 | |
| WO | 2006005706 A2 | 1/2006 | |
| WO | 2007047967 A2 | 4/2007 | |
| WO | 2008116293 A2 | 10/2008 | |
| WO | WO 2010/057882 | * | 5/2010 |
| WO | 2010062570 A2 | 6/2010 | |
| WO | 2011137886 A1 | 11/2011 | |
| WO | 2011147797 A2 | 12/2011 | |
| WO | 2013150126 A2 | 10/2013 | |
| WO | 2013150127 A2 | 10/2013 | |

OTHER PUBLICATIONS

Stains Cliff I et al: "Molecules that target beta-amyloid", Chemmedchem, Wiley—VCH Verlag., Weinheim, DE, vol. 2, No. 12, Dec. 1, 2007 (Dec. 1, 2007), pp. 1675-1692.

Funke Susanne Aileen et al: "Peptides for Therapy and Diagnosis of Alzheimer's Disease", Current Pharmaceutical Design, Bentham Science Publishers, NL, vol. 18, No. 6, Feb. 1, 2012 (Feb. 1, 2012), pp. 755-767.

Ranjini K. Sundaram et al: "Novel Detox Gel Depot Sequesters [beta]-Amyloid Peptides in a Mouse Model of Alzheimer's Disease", International Journal of Peptide Research and Therapeutics, vol. 18, No. 2, Nov. 23, 2011 (Nov. 23, 2011), pp. 99-106.

Andreas Müller-Schiffmann et al: "Combining Independent Drug Classes into Superior, Synergistically Acting Hybrid Molecules", Angewandte Chemie International Edition, vol. 49, No. 46, Nov. 8, 2010 (Nov. 8, 2010), pp. 8743-8746.

Dirk Bartnik et al: "Differently selected D-enantiomeric peptides act on different A.beta. species", Rejuvenation Research, Mary Ann Liebert, New Rochelle, NY, US, vol. 13, No. 2-3, May 12, 2010 (May 12, 2010), pp. 202-205.

Susanne Aileen Funke et al: "Mirror image phage display—a method to generate d-peptide ligands for use in diagnostic or therapeutical applications", Molecular Biosystems, vol. 5, No. 8, Jan. 1, 2009 (Jan. 1, 2009), p. 783.

Thomas Van Groen et al: "Reduction of Alzheimer's Disease Amyloid Plaque Load in Transgenic Mice by D3, a D-Enantlomertc Peptide Identified by Mirror Image Phage Display",Chemmedchem, Bd. 3, Nr. 12, Dec. 15, 2008 (Dec. 15, 2008), pp. 1848-1852.

Hongmei Liu et al: "Transport of Alzheimer Disease Amyloid-b-Bindlng d-Amino Acid Peptides across an In Vitro Bood-Brain Barrier Model", Dec. 2, 2009 (Dec. 2, 2009), found on Internet:URL:http://online.liebertpub.com/dol/pdf/10.1089/rej.2009.0926 (accessed on Jan. 7, 2016).

Susanne Aileen Funke et al: "Oral Treatment with the D-Enantiomeric Peptide D3 Improves the Pathology and Behavior of Alzheimer's Disease Transgenic Mice", ACS Chemical Neuroscience, vol. 1 No. 9 Sep. 15, 2010 (Sep. 15, 2010), pp. 639-648.

Liu Ming et al., Progress in soluble AA oligomers in Alzheimer's disease and drugs targeting AA oligomers, Chinese Pharmacological Bulletin, vol. 24, No. 12, pp. 1554-1557, Dec. 2008.

Olujide O.Olubiyi et al., Structures of the Amyloid . . . ,The Journal of Physical Chemistry, vol. 116, p. 3280-3291, Feb. 2, 2012.

* cited by examiner

```
                         SEQUENCE LISTING

<160> NUMBER OF SEQ ID NOS: 79

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 1

Arg Pro Arg Thr Arg Leu Arg Thr His Gln Asn Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 2

Lys Gln His His Val Glu Tyr Gly Ser Asp His Arg Phe Glu Ala Asp
1               5                   10                  15
```

```
<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 3

Ser His Tyr Arg His Ile Ser Pro
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 4

Gly Ile Ser Trp Gln Gln Ser His His Leu Val Ala
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 5

Pro Arg Thr Arg Leu His Thr His
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 6

Gln Ser His Tyr Arg His Ile Ser Pro Ala Gln Val
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 7

Gln Ser His Tyr Arg His Ile Ser Pro Asp Gln Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 8
```

```
Gln Ser His Tyr Arg His Ile Ser Pro Ala Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 9

Lys Ser His Tyr Arg His Ile Ser Pro Ala Lys Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 10

Arg Pro Arg Thr Arg Leu His Thr His Arg Asn Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 11

Arg Pro Arg Thr Arg Leu His Thr His Arg Thr Glu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 12

Lys Pro Arg Thr Arg Leu His Thr His Arg Asn Arg
1               5                   10

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 13

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 14
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 14

Arg Pro Arg Thr Arg Leu His Thr His Arg Asn Arg Asn Trp Asn Arg
1               5                   10                  15

Pro Arg Thr Arg Leu His Thr His Arg Asn Arg
            20                  25

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ntermini (rprtrlhthrnr)2-PEG3

<400> SEQUENCE: 15

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ctermini: PEG5-(rprtrlhthrnr)2

<400> SEQUENCE: 16

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 17

Asp Ala Glu Phe Arg His Asp Ser Gly Tyr Glu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 18

His His Gly His Ser Pro Asn Val Ser Gln Val Arg
```

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 19

Gly Ser Phe Ser Thr Gln Val Gly Ser Leu His Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 20

His Thr Gly Thr Gln Ser Tyr Val Pro Arg Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 21

Thr Leu Ala Tyr Ala Arg Ala Tyr Met Val Ala Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 22

Thr Leu Ala Tyr Ala Arg Ala Tyr Met Val Ala Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 23

Ala Thr Pro Gln Asn Asp Leu Lys Thr Phe Pro His
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic D-Peptide

<400> SEQUENCE: 24

Thr Gln Pro Glu Thr Asp Leu Leu Arg Val Gln Phe
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 25

Cys Ile Thr Trp Pro Pro Thr Gly Leu Thr Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 26

Thr Phe Leu Glu Thr Gly Pro Ile Tyr Ala Asp Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 27

Leu Val Pro Pro Thr His Arg His Trp Pro Val Thr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 28

Ala Pro Pro Gly Asn Trp Arg Asn Tyr Leu Met Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 29

Asp Asn Tyr Ser Asn Tyr Val Pro Gly Thr Lys Pro
1               5                   10

<210> SEQ ID NO 30

```
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 30

Ser Val Ser Val Gly Met Lys Pro Ser Pro Arg Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 31

Ser Leu Pro Asn Pro Phe Ser Val Ser Ser Phe Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 32

Tyr Val His Asn Pro Tyr His Leu Pro Asn Pro Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 33

Cys Arg Arg Leu His Thr Tyr Ile Gly Pro Val Thr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 34

Gly Ala Thr Met Lys Lys Met Asp Asp His Thr Val
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 35
```

```
Leu Gly Lys Thr Gln Lys Leu Ser Asp Ala His Ser
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 36

```
Asp Asp Gln Ala Arg Pro Tyr Met Ala Tyr Gly Pro
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 37

```
Gly Asp Thr Trp Val Asn Met Val Ser Met Val His
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 38

```
Gly Tyr Thr Trp Val Asn Met Val Ser Met Val His
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 39

```
Trp Thr Asn Thr Val Ala Arg Leu Ala Thr Pro Tyr
1               5                   10
```

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 40

```
Gln Thr Gln Ala Leu Tyr His Ser Arg Gln Val His
1               5                   10
```

<210> SEQ ID NO 41
<211> LENGTH: 12
<212> TYPE: PRT
<213> ORGANISM: Artificial Sequence
<220> FEATURE:

```
<223> OTHER INFORMATION: Description of Artificial Sequence: Synthetic
      D-Peptide

<400> SEQUENCE: 41

Asn Ser Gln Thr Gln Thr Leu His Leu Phe Pro His
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 42

His Asn Thr Ser Ala Asn Ile Leu His Ser Ser His
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 43

Ser His Ile Asn Pro Thr Ser Phe Trp Pro Ala Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 44

Thr Phe Ser Asn Pro Leu Tyr Met Trp Pro Arg Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 45

Gly Pro Ser Pro Phe Asn Pro Gln Pro Thr Pro Val
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 46

Phe Ser Asp His Lys Ser Pro Thr Pro Pro Arg
1               5                   10
```

```
<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 47

Ser Thr Ser Val Tyr Pro Pro Pro Pro Ser Ala Trp
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 48

Tyr Gly Leu Pro Thr Gln Ala Asn Ser Met Gln Leu
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 49

His Asn Arg Thr Asp Asn Thr Tyr Ile Arg Pro Thr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 50

Leu Gln Gln Pro Leu Gly Asn Asn Arg Pro Asn Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 51

Lys Pro Glu Asp Ser Ala Ala Tyr Pro Gln Asn Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 52
```

```
Arg Pro Glu Asp Ser Val Ile Thr Lys Thr Gln Asn Thr
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 53

```
Arg Ala Ala Asp Ser Gly Cys Thr Pro Thr Lys His
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 54

```
Arg Pro Arg Thr Arg Leu His Thr His Arg Asn Thr
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 55

```
Arg Pro Arg Thr Arg Leu His Thr His Thr Asn Val
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 56

```
Arg Pro Arg Thr Arg Leu His Thr His Thr Asn Arg
1               5                   10
```

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 57

```
Arg Pro Arg Thr Arg Leu His Thr His Arg Lys Gln
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 58

Arg Pro Arg Thr Arg Leu His Thr Leu Arg Asn Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 59

Arg Arg Arg Ser Pro Leu His Thr His Arg Asn Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 60

Leu Arg Ser Pro Arg Gln Arg Arg Ile Pro Arg Ile
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 61

Arg Lys Arg Gln Leu Arg Met Thr Thr Pro Arg Pro
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 62

Ser His Tyr Arg His Ile Ser Pro Ala Gln Lys
1               5                   10

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ntermini (rprtrlhthrnr)2

<400> SEQUENCE: 63

Arg Pro Arg Thr Arg Leu His Thr His Arg Asn Arg Arg Pro Arg Thr

```
                1               5                  10                    15
Arg Leu His Thr His Arg Asn Arg
            20

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ctermini: (rprtrlhthrnr)2

<400> SEQUENCE: 64

Arg Pro Arg Thr Arg Leu His Thr His Arg Asn Arg Arg Pro Arg Thr
1               5                  10                  15

Arg Leu His Thr His Arg Asn Arg
            20

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 65

Arg Pro Ile Thr Arg Leu Arg Thr His Gln Asn Arg
1               5                  10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 66

Pro Thr Leu His Thr His Asn Arg Arg Arg Arg Arg
1               5                  10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 67

Pro Asn His His Arg Arg Arg Arg Arg Thr Thr Leu
1               5                  10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 68

Arg Arg Pro Thr Leu Arg His Thr His Asn Arg Arg
1               5                  10
```

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 69

Arg Pro Arg Thr Arg Leu Arg Asn Arg
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 70

Arg Pro Arg Thr Arg Leu
1               5

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 71

Arg Pro Ile Thr Arg Leu His Thr Asp Arg Asn Arg
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 72

Arg Pro Ile Thr Thr Leu Gln Thr His Gln Asn Arg
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 73

Arg Pro Arg Thr Arg Leu His Thr His Arg Asn Arg
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 74

Arg Pro Ile Thr Arg Leu Gln Thr His Glu Gln Arg
1               5                   10

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 75

Arg Pro Arg Thr Arg Leu Arg Asn Arg Arg Pro Arg Thr Arg Leu Arg
1               5                   10                  15

Asn Arg

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 76

Pro Thr Leu His Thr His Asn Arg Arg Arg Arg Pro Thr Leu His
1               5                   10                  15

Thr His Asn Arg Arg Arg Arg Arg
            20

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 77

Ser Gly Trp His Tyr Asn Trp Gln Tyr Trp Trp Lys
1               5                   10

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 78

Arg Pro Arg Thr Arg Ser Gly Trp His Tyr Asn Trp Gln Tyr Trp Trp
1               5                   10                  15

Lys Arg Asn Arg
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      D-Peptide

```
<400> SEQUENCE: 79

Pro Thr Leu Ser Gly Trp His Tyr Asn Trp Gln Tyr Trp Trp Lys Arg
1               5                   10                  15

Arg Arg Arg Arg
            20
```

METHOD FOR TREATING BLOOD, BLOOD PRODUCTS AND ORGANS

SEQUENCE LISTING

The instant application contains a Sequence Listing which has been submitted electronically in ASCII format and is hereby incorporated by reference in its entirety. Said ASCII copy, created on Feb. 9, 2015, is named Sequ List clean corrected version ASCII 09 02 2015 FZJ1205PCTUS and is 12,678 bytes in size.

BACKGROUND OF THE INVENTION

1. Field of the Invention

The present invention relates to a method for treating (ex vivo) blood, blood products and organs for preventing the transmission of Alzheimer's disease and other amyloid-based diseases.

2. Discussion of Background Information

On account of the demographic development within the next few decades, the number of people suffering from age-related diseases will increase. Mention is to be made here in particular of so-called Alzheimer's disease (AD, Alzheimer dementia, Latin=Morbus Alzheimer).

One feature of Alzheimer's disease is extracellular deposits of the amyloid-beta peptide (A-beta peptide, Aβ, or Aβ peptide). This deposition of the A-beta peptide in plaques is typically determined in the brains of AD patients post mortem. Consequently, various forms of the A-beta peptide—such as e.g. fibrils—are deemed to be responsible for the onset and the progress of the diseases. Additionally, for some years, the small, freely diffusible A-beta oligomers have been considered to be primary causes of the onset and the progress of AD. A-beta monomers, as building blocks of the A-beta oligomers are continually formed in the human body and are presumably per se nontoxic. A-beta monomers can inadvertently cluster depending on their concentration. The concentration is dependent on their formation and degradation rate in the body. If an increase in the concentration of A-beta monomers takes place in the body with increasing age, a spontaneous clustering of the monomers to A-beta oligomers is all the more probable. The A-beta oligomers thus formed could replicate analogously to the prions and ultimately lead to Alzheimer's disease.

An important difference between prevention and treatment or even healing of AD lies in the fact that prevention can be achieved merely by preventing the formation of the first A-beta oligomers. For this, a few A-beta ligands are sufficient which have lower affinity and are less selective as regards the A-beta oligomers.

The formation of the A-beta oligomers from many monomers is a reaction of high order and thus dependent to a high degree on the A-beta monomer concentration. Consequently, even a small reduction in the active A-beta monomer concentration leads to a prevention of the formation of the first A-beta oligomers. This mechanism has hitherto been the basis of prevention.

When treating AD, however, a completely altered situation is assumed. This is because here A-beta oligomers or possibly also even larger polymers or fibrils are present which have formed by the prion-like replication of the oligomers. However, this is a reaction of low order and barely dependent on the A-beta monomer concentration.

Hitherto, no approved medicament exists for a causal treatment of Alzheimer dementia (AD). Typically, deposits of the so-called beta-amyloid peptide (Aβ or A-beta) are found in plaques in the brains of AD patients post mortem. Consequently, various forms of the Aβ oligomers, e.g. fibrils, have for a long time already been considered to be responsible for the onset and the progress of AD. For a few years, particularly the small, freely diffusible Aβ oligomers have been held responsible as the main causes of the onset and the progress of AD. Aβ monomers are continuously formed in the human body and are presumably per se nontoxic. It is speculated whether Aβ monomers inadvertently cluster as a function of their concentration and thus with increasing age ever more probably spontaneously to give Aβ oligomers. Aβ oligomers, once formed, could replicate by means of a prion-like mechanism and ultimately lead to the disease. For some time, it has been discussed whether AD—similarly to prion diseases—is in principle transmissible from person to person. The same applies to all amyloid-associated diseases (e.g. Parkinson's). In particular, a possible transmission by means of blood transfusion, administration of blood products and organ transplants could lead, without suitable tests and prevention methods, to a massive risk to the health of recipients. In this connection, there has been a report in the nonscientific literature of the premature onset of AD in a transgenic mouse after its complete blood was exchanged for that of a diseased mouse.

On account of these considerations, it should be an option to free blood, blood products and organs from infectious particles by means of (prophylactic or preventative) treatment, or to deactivate these. It should in this connection be the aim to entirely remove or to destroy, i.e. to detoxify, toxic Aβ oligomers and to thereby prevent their prion-like replication.

The prior art discloses various methods for eliminating biohazardous materials, bioparticles, molecules and pathological protein deposits. For example, there is research according to which nanomagnets are used in order to purify blood in a targeted manner from a hazardous material within a few minutes. Similarly, it has been described to remove LDL cholesterol from the blood by means of direct absorption of lipoproteins (DALI).

The immobilization of antibodies or peptides is described in DE 600 26 983 T2 or U.S. Pat. No. 5,968,820.

Furthermore, DE 102009037015 A1 discloses a device and a method for eliminating biohazardous substances from body fluids. The isolation of cells, bioparticles and molecules from liquids is described in DE 102005063175 A1. Furthermore, DE 102005031429 A1 discloses a method for the selective determination of pathological protein deposits. Finally, DE 102005009909 A1 describes compounds for treating diseases in connection with incorrectly folded proteins.

The substances known from the prior art reduce the concentration of A-beta monomers and/or oligomers in a very wide variety of ways. Thus, e.g. gamma-secretase modulators are known which were used in animal experiments for prevention.

WO 02/081505 and DE 101 17 281 A1 discloses various sequences of D-amino acids which bind to A-beta peptides. These sequences in WO 02/081505 from D-amino acids bind to amyloid-beta peptides with a dissociation constant $K_D$ value of 4 μM.

WO 2011/147797 discloses hybrid compounds consisting of aminopyrazoles and peptides which prevent A-beta oligomerization.

A use of these compounds for purifying blood, blood products and/or organs, however, is not disclosed.

For many substances which have shown positive results in animal experiments, this effect could not be confirmed in clinical studies on humans. In phase II and III clinical studies, only people diagnosed with clear AD are allowed to be treated. Here, a slight decrease in the A-beta monomer concentration no longer suffices to prevent larger amounts of A-beta oligomers, and/or to influence the course of the disease.

Hitherto, Alzheimer dementia has primarily been diagnosed by neuropsychological tests, by experiments on people in which the symptoms were already recognized. However, it is known that A-beta oligomers and the subsequent fibrils and plaques are formed up to 20 years before the onset of the symptoms in the brain of the patients, and may have already caused irreversible damage. However, there is hitherto still no possibility of diagnosing AD before the onset of symptoms.

It is now an object of the present invention to free blood, blood products and/or organs by treatment of toxic and/or infectious particles, or to deactivate these. It is the aim to completely remove the Aβ oligomers present in blood, blood products or organs, or to convert them to nonharmful forms.

SUMMARY OF THE INVENTION

Accordingly, the invention provides methods for treating (in vitro, ex vivo) blood, blood products and/or organs, characterized in that the blood, the blood products and/or organs are removed from the human or animal body and amyloid-beta oligomers are removed and/or detoxified.

The treated blood can originate from a blood bank and/or be stored in a blood bank after treatment.

Furthermore, it is possible to use the method according to the invention preventatively in healthy people. Here, the blood of these people who have no AD symptoms is freed from any amyloid-beta oligomers present, without reference to method steps for the therapeutic treatment of the human or animal body.

The Aβ oligomers can be removed by e.g. adding beads to the blood which bind or retain Aβ oligomers. For treating blood samples, the substances binding Aβ oligomers can be bonded for this purpose to magnetic beads. One example of beads is Dynabeads from Dynal. Dynabeads® M-280 streptavidin (Dynal A.S., Oslo) are supramagnetic microbeads which are covalently bonded with purified streptavidin which binds biotin with high affinity ($K_D=10^{-15}$). Subsequently, these beads can be removed again with the Aβ oligomers bonded thereto, e.g. by affinity chromatography, filtration, size exclusion sedimentation or centrifugation.

In one variant of the invention, the Aβ oligomers can be removed by passing the blood and/or the blood sample over a surface which binds or retains Aβ oligomers. According to the invention, the molecules which bind or detoxify Aβ oligomer (so-called capture molecules) can be arranged on a support, over which the liquid sample is passed. In one variant, an immobilization with the help of nanomagnets is also possible for the capture molecules. Similarly, the arrangement of the capture molecules in a dialysis system is possible. In a further variant, the capture molecules can consist of a biocompatible material. Supports can also be membranes, filters, filter sponges, beads, rods, cords, columns and hollow fibers.

In a further variant relating to organs, the Aβ oligomers can be removed by passing the capture molecules over and/or through an organ (in vitro/ex vivo).

In a further variant of the invention, Aβ oligomers can be deactivated by adding a substance which converts Aβ oligomers into nontoxic, non-amyloidogenic, noninfectious forms.

Aβ-oligomer-deactivating substances or Aβ-oligomer-binding substances that can be used are all Aβ-oligomer-modifying ligands, e.g. Aβ antibodies or Aβ-binding peptides. The substances to be used should have the highest possible affinity to Aβ oligomers. The corresponding dissociation constant should be in the µM range, preferably nM range, in particular pM range or even lower. Since the target molecule of the therapeutic treatment is an Aβ oligomer and thus naturally a multivalent target, in one variant of the invention for the treatment, the substance to be used can be prepared from several copies of an already efficiently Aβ-oligomer-binding unit. In the absence troublesome influences (e.g. as a result of steric hindering), an n-mer of an Aβ oligomer-binding unit which binds to Aβ oligomer with a dissociation constant ($K_D$) of at least x, an apparent K of $x^n$ can be achieved. In order to achieve this, there are various options: the Aβ-oligomer-binding units (monomer units) can be linked together covalently or noncovalently (e.g. a biotin group or a streptavidin tetramer). In one variant of the invention, as many copies as desired can be immobilized on the surface of beads.

In the context of the present invention, the term A-beta oligomers refers to both A-beta aggregates and A-beta oligomers and also small freely diffusing A-beta oligomers. In the context of the invention, oligomer is a polymer formed from 2, 3, 4, 5, 6, 7, 8, 9, 10, 11, 12, 13, 14, 15, 16, 17, 18, 19 or 20 monomers or multiples thereof.

The present method is preferably carried out outside of the human or animal body. The terms used for this are in vitro or ex vivo.

In one embodiment, the polymers are peptides. These consist preferably essentially of D-amino acids.

In the context of the present invention, the term "essentially of D-amino acids" means that the monomers to be used are composed at least 60%, preferably 75%, 80%, particularly preferably 85%, 90%, 95%, in particular 96%, 97%, 98%, 99%, 100%, of D-amino acids.

In one variant of the invention, monomers are used which bind to an A-beta monomer and/or A-beta oligomers and/or fibrils of the A-beta peptide with a dissociation constant ($K_D$ value) of at most 500 µM, preferably 250, 100, 50 µM, particularly preferably 25, 10, 6 µM, in particular 4 µM.

The polymer comprises 2, 3, 4, 5, 6, 7, 8, 9, 10 or more of the monomers described above.

In a further embodiment, the monomers are selected from the group consisting of:
SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79, and homologs thereof.

In a further variant, the polymers bind to the multimerization domain of the amyloid beta-peptide.

The term "multimerization domain" defines those domains of the amyloid beta-peptide which have to do with the interaction of the amyloid beta-peptides with one another. In one variant, the amino acids 10-42 of the amyloid beta-peptide fulfill this function.

In a further variant, the monomers have sequences which differ from the stated sequences by up to three amino acids.

Furthermore, the monomers used are also sequences which contain the aforementioned sequences.

In a further variant, the monomers have fragments of the aforementioned sequences or have homologous sequences to the aforementioned sequences.

In the context of the invention, "homologous sequences" or "homologs" means that an amino acid sequence has an identity with one of the aforementioned amino acid sequences of the monomers of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%. Instead of the term "identity", in the present description the terms "homologous" or "homology" are used synonymously. The identity between two nucleic acid sequences or polypeptide sequences is calculated by comparison with the help of the program BESTFIT based on the algorithm from Smith, T. F. and Waterman, M. S (Adv. Appl. Math. 2: 482-489 (1981)), with adjustment of the following parameters for amino acids: Gap creation penalty: 8 and Gap extension penalty: 2; and the following parameters for nucleic acids: Gap creation penalty: 50 and Gap extension penalty: 3. Preferably, the identity between two nucleic acid sequences or polypeptide sequences is defined by the identity of the nucleic acid sequence/polypeptide sequence over the particular overall sequence length, as is calculated by comparison with the help of the program GAP based on the algorithm from Needleman, S. B. and Wunsch, C. D. (J. Mol. Biol. 48: 443-453), with adjustment of the following parameters for amino acids: Gap creation penalty: 8 and Gap extension penalty: 2; and the following parameters for nucleic acids: Gap creation penalty: 50 and Gap extension penalty: 3.

In the context of the present invention, two amino acid sequences are identical if they have the same amino acid sequence.

In one variant, homologs are to be understood as meaning the corresponding retro-inverse sequences of the aforementioned monomers. According to the invention, the term "retro-inverse sequence" is used to refer to an amino acid sequence which is composed of amino acids in the enantiomeric form (inverse: chirality of the alpha carbon atom inverted) and in which additionally the sequence order has been reversed compared to the original amino acid sequence (retro=backwards).

The polymer is composed of identical monomers, or comprises different monomers.

In one alternative, the polymer is composed of any desired combination of 2, 3, 4, 5, 6, 7, 8, 9, 10 or more of the monomers described above.

In one embodiment, the polymer is a dimer of two D3 monomers (SEQ ID NO:13).

In one embodiment, the polymer is a dimer of two RD2 monomers (RD 2-RD 2: ptlhthnrrrrrptlhthnrrrrr (SEQ ID NO:76).

Dimers can for example be prepared via chemical synthesis or peptide synthesis.

In one embodiment of the invention, the monomers are covalently linked with one another. In a further embodiment, the monomers are not covalently linked with one another.

A covalent bond or linkage of the monomer units in the context of the invention is present if the peptides are linked together linearly head to head, tail to tail or head to head without linkers or linker groups being used in between.

A noncovalent linkage in the context of the invention is present if the monomers are linked together via biotin and streptavidin, in particular streptavidin tetramer.

A covalent linkage can be achieved by linearly coupling the monomer units head to head, tail to tail or head to tail, in each case without linkers or with a linker group. In an alternative, a linkage in a tree-like structure (dendrimers) on a platform molecule or a combination of these options is also possible. Here, nonidentical monomer units can also be combined.

The polymer is characterized in that it binds amyloid-beta oligomers with a dissociation constant of at most 1 mM, preferably 800, 600, 400, 200, 100, 10 µM, particularly preferably 1000, 900, 800, 700, 600, 500, 400, 300, 200, 100, 50 nM, especially preferably 1000, 900, 800, 700, 600, 500, 400, 300, 200, 100, 50 pM, most preferably at most 20 pM.

The polymer is suitable for use in medicine.

In one embodiment, it is a polymer which can be used for treating Alzheimer's disease. In a further embodiment, it is a polymer which can be used for treating Parkinson's disease, Creutzfeldt Jakob disease (CJD), scrapie, bovine spongiform encephalopathy (BSE), or diabetes.

The constructed polymers of monomers which for their part bind to A-beta oligomers show clear, synergistic effects with regard to their selectivity and affinity to the A-beta oligomers compared to the monomers. In other words, the polymers according to the invention are superior to the monomers. Synergistic effects in the context of the present invention are effects which exhibit a higher selectivity and affinity with regard to the A-beta oligomers, in particular the $K_D$ value regarding the binding to A-beta oligomers than the monomers individually or in their addition.

A linker is to be understood as meaning one or more molecules which are bonded to the monomers via covalent bonds, it also being possible for these linkers to be linked with one another by covalent bonds.

In an alternative of the present invention, the properties of the polymer pregiven by the monomers, namely the binding to A-beta oligomers, are not changed by the linkers.

In a further alternative, the linkers bring about a change in the properties of the polymer which are pregiven by the monomers. In one such embodiment, the selectivity and/or affinity of the polymers according to the invention as regards the A-beta oligomers is increased and/or the dissociation constant is reduced. In a further embodiment, the linkers are selected, or can be arranged, such that they change the steric effect of the polymers according to the invention in such a way that these bind only selectively to A-beta oligomers of a certain size. Such a change in the steric effect of the polymers according to the invention can also be achieved by means of building up branched polymers according to the invention, by dendrimers of a particular structure or the corresponding structure of the polymer by means of monomers and a platform molecule or combinations of these options.

The invention further provides a composition, and use thereof, for determining Alzheimer's disease, in which the D-peptide a) comprises a retro-inverse sequence of the amyloid beta-peptide or amyloid beta-peptide part fragments and consists completely of D-amino acids and/or
b) binds to the multimerization domain of the amyloid beta-peptide and/or
c) comprises or has the sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 and consists completely of D-amino acids and/or
d) comprises or has D-peptides with the sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 where the D-peptides partly comprise L-amino acids and/or
e) comprises or has homologous sequences to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79.

In one variant, "D-peptides" consist of a retro-inverse sequence to the amyloid beta-peptide or amyloid beta-peptide part fragments and completely of D-amino acids.

A "part fragment" consists of 3, 4, 5, 6, 7, 8, 9, 10, 11, 12, 13, 14, 15, 16 or more amino acids homologous to the amino acid sequence of the amyloid beta-peptide.

In a further variant, the D-peptides bind to the multimerization domain of the amyloid beta-peptide. In a further variant, the D-peptides have the sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 and consist completely of D-amino acids. In a further variant, the D-peptides have one of the aforementioned sequences, and comprise partly L-amino acids. In a further variant, the D-peptides have homologous sequences to the aforementioned sequences. "D-peptide" is understood as meaning a peptide which is composed of amino acids in the D form.

In a variant of the invention, the D-peptides also have partly L-amino acids. "Partly" L-amino acids means that 1, 2, 3, 4, 5, 6, 7, 8, 9, 10 or more amino acids homologous to the amino acid sequence of the D-peptide consisting of D-amino acids are replaced by in each case the same amino acid in the L conformation.

In one variant, "D-peptides" consist of a retro-inverse sequence to the amyloid beta-peptide or amyloid beta-peptide part fragments and completely of D-amino acids.

A "part fragment" consists of 3, 4, 5, 6, 7, 8, 9, 10, 11, 12, 13, 14, 15, 16 or more amino acids homologous to the amino acid sequence of the amyloid beta-peptide.

In a further variant, the D-peptides according to the invention bind to the multimerization domain of the amyloid beta-peptide. In a further variant, the D-peptides have the aforementioned sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 and consist completely of D-amino acids.

In another embodiment of the present invention, the peptide comprises the sequence motif DB 4: RPRTRLRTHQNR (SEQ ID NO:1) or active fragments thereof.

In another embodiment of the present invention, the peptide comprises the sequence motif SHYRHISP (SEQ ID NO:3) or active fragments thereof.

In a further embodiment of the present invention, the peptide comprises the sequence motif GISWQQSHHLVA (SEQ ID NO:4) or active fragments thereof.

In a further embodiment of the present invention, the peptide comprises the sequence motif PRTRLHTH (SEQ ID NO:5) or active fragments thereof.

In a further variant, the peptide is selected from the group consisting of peptides with the D-amino acid sequences: a) QSHYRHISPAQV (SEQ ID NO:6); b) QSHYRHISPDQV (SEQ ID NO:7); c) QSHYRHISPAR (SEQ ID NO:8); d) KSHYRHISPAKV (SEQ ID NO:9); e) RPRTRLHTHRNR (SEQ ID NO:10); i) RPRTRLHTHRTE (SEQ ID NO:11); and g) KPRTRLHTHRNR (SEQ ID NO:12); preference is also given to sequences which differ from the sequences a) to g) by up to three amino acids; and also sequences which comprise the sequences a) to g), and sequences which differ from the sequences a) to g) by up to three amino acids.

In a further variant, the peptide is selected from the group consisting of peptides with the D-amino acid sequences: D3D3: rprtrlhthrnrrprtrlhthrnr (SEQ ID NO:13), aD3nwnD3: rprtrlhthrnrnwnrprtrlhthrnr (SEQ ID NO:14), double-D3-free-Ntermini: (rprtrlhthrnr)2-PEG3 (SEQ ID NO:15), double-D3-free-Ctermini: PEG5-(rprtrlhthrnr)2 (SEQ ID NO:16), or double-D3-free-Ntermini: (rprtrlhthrnr)2-(SEQ ID NO:63), double-D3-free-Ctermini: (rprtrlhthrnr)2 (SEQ ID NO:64), DB 3: rpitrlrthqnr (SEQ ID NO: 65), RD 2: ptlhthnrrrrr (SEQ ID NO: 66), RD 1: pnhhrrrrrrtl (SEQ ID NO: 67), RD 3: rrptlrhthnrr (SEQ ID NO: 68), D3-delta-hth: rprtrlrnr (SEQ ID NO:69), NT-D3: rprtrl (SEQ ID NO: 70), DB 1: rpitrlhtnrnr (SEQ ID NO: 71), DB 2: rpittlqthqnr (SEQ ID NO: 72), DB 5: rpitrlqtheqr (SEQ ID NO. 74), D3-delta-hth D3-delta-hth: rprtrlrnrrprtrlrnr (SEQ ID NO:75), RD 2-RD 2: ptlhthnrrrrrptlhthnrrrrr (SEQ ID NO: 76), DO 3: sgwhynwqywwk (SEQ ID NO:77), rprtrsgwhynwqywwkrnr (SEQ ID NO:78) and ptlsgwhynwqywwkrrrrr (SEQ ID NO:79).

Preference is also given to sequences which differ from the aforementioned sequences by up to three amino acids; and also sequences which comprise each individual or each arbitrary combination of the aforementioned sequences.

In a further variant, the D-peptides have fragments of the aforementioned sequences and have homologous sequences to the aforementioned sequences.

According to the invention, defined, homogeneous and stable preparations of standards can also be used for quantifying pathogenic aggregates or oligomers from proteins endogenous to the body, in particular for treating blood, blood products and/or organs. Here, it is possible to use standards for quantifying oligomers or pathogenic aggregates which characterize a protein aggregation disease or an amyloid degeneration or protein multifolding disease. Here, a polymer is constructed from polypeptide sequences which are identical as regards their sequence in the corresponding part region with the proteins endogenous to the body, or have a homology of at least 50% over the corresponding part region with the proteins endogenous to the body which characterize a protein aggregation disease or an amyloid degeneration or protein misfolding disease, where the polymers do not aggregate.

In the context of the present invention, standard is used to refer to a generally valid and accepted, established reference parameter which serves for the comparison and determination of properties and/or amount, in particular for determining the parameter and amount of pathogenic aggregates from proteins endogenous to the body. The standard in the context of the present invention can be used for calibrating instruments and/or measurements.

In the context of the present invention, the term "protein aggregation disease" can also include amyloid degenerations and protein misfolding diseases. Examples of such diseases and the associated proteins endogenous to the body are: A-beta and tau protein for AD, alpha-synuclein for Parkinson's disease, amylin for diabetes or prion protein for prion diseases, for example such as human Creutzfeldt Jakob disease (CJD), the sheep's disease scrapie and bovine spongiform encephalopathy (BSE).

The term "corresponding part region" of proteins endogenous to the body is to be understood as meaning the peptide sequence which, according to the definitions according to the invention, has an identical peptide sequence, or a peptide sequence homologous with the stated percentage, of a monomer from which the standards according to the invention are constructed.

It is essential for the standards according to the invention that the standards do not aggregate, preferably as a result of the use of monomeric sequences which do not aggregate since the "corresponding part region" of endogenous proteins is not responsible for the aggregation, or which do not aggregate as a result of blocking the groups responsible for the aggregation.

Aggregates in the context of the present invention are
  particles which consist of a plurality of preferably identical building blocks which are not covalently bonded together and/or
  noncovalent clusters of a plurality of monomers.

In one embodiment of the present invention, the standards have a precisely defined number of epitopes which are covalently bonded together (directly or via amino acids, spacers and/or functional groups) for the binding of the corresponding probes.

Probes in the context of the invention are selected from the group consisting of: antibodies, nanobody or affibody.

The number of epitopes is determined by using a polypeptide sequence which, as regards its sequence, is identical to the part region of the endogenous proteins which forms an epitope and/or has a homology of at least 50% with this part region, and in so doing has the biological activity of the epitope.

In a further embodiment of the present invention, the epitopes are epitopes of the A-beta peptide selected from the part regions A-beta 1-11, A-beta 3-11 or pyroGluA-beta 3-11, for example of the human N-terminal epitope (with the following sequence: DAEFRHDSGYE (1-11) (SEQ ID NO:17)).

The standard molecule according to the invention is a polymer of the polypeptide sequences defined above. In the context of the invention, oligomer is a polymer of 2, 3, 4, 5, 6, 7, 8, 9, 10, 11, 12, 13, 14, 15, 16, 17, 18, 19 or 20 monomers (monomer is understood as meaning the aforementioned polypeptide sequence), or multiples thereof, preferably 2-16, 4-16, 8-16, particularly preferably 8 or 16, or multiples thereof.

In one alternative of the present invention, the standards are water-soluble.

In one alternative of the present invention, the standards are made up of identical polypeptide sequences.

In a further alternative of the present invention, the standards are made up of different polypeptide sequences.

In one alternative of the present invention, those above-defined polypeptide sequences are aligned in a linear conformation.

In one alternative of the present invention, those above-defined polypeptide sequences are aligned to give a branched oligomer according to the invention.

In one alternative of the present invention, those above-defined polypeptide sequences are aligned to give a cross-linked oligomer according to the invention.

Branched or crosslinked oligomers according to the invention can be prepared by linking individual building blocks by means of lysine or by means of click chemistry.

In one alternative, the invention relates to a standard molecule comprising or made up of copies of the amino-terminal part of the A-beta peptide selected from the part regions A-beta 1-11, A-beta 3-11, or pyroGluA-beta 3-11, for example of the human N-terminal epitope (with the following sequence: DAEFRHDSGYE (1-11) (SEQ ID NO:17)).

The copying of the epitopes by functional groups can be carried out before or after the synthesis of the individual building blocks. The covalent linking of the polypeptide sequences is characteristic of the standards according to the invention.

The polypeptide sequences to be used according to the invention can be identical to the sequence of the A-beta full-length peptide or exhibit a homology of 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 100% with the sequence of the A-beta full-length peptide.

Alternatively, for constructing the standard molecules according to the invention, polypeptide sequences are also used which are identical to a part region of the A-beta full-length peptide, or exhibit a homology of 50, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% with a part region of the A-beta full-length peptide.

Of essential importance for the sequences used according to the invention is their property not to aggregate (or to aggregate only in a controlled manner according to the conditions) and/or their the activity as epitope.

In a further embodiment of the present invention, the standards are constructed as dendrimers. The dendrimers according to the invention are made up of the above-described polypeptide sequences to be used according to the invention and can contain a central backbone molecule.

In one variant, the dendrimers according to the invention contain polypeptide sequences which have a sequence which is identical to a part region of the A-beta peptide, or exhibits an at least 50% homology to the corresponding part region.

According to the invention, the term "at least 50% homology" is also to be understood as meaning a higher homology, selected from the group consisting of 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%.

Standards, advantageously with a higher solubility under aqueous conditions than pathogenic aggregates or oligomers from endogenous proteins, are formed in one embodiment of the invention from polypeptide sequences which are identical to the N-terminal region of the A-beta peptide or have at least 50% homology thereto. According to the invention, the N-terminal region of a A-beta polypeptide is to be understood as meaning the amino acid sequence A-beta 1-8, A-beta 1-11, A-beta 1-16, A-beta 3-11 or pyroGluA-beta 3-11.

A standard molecule that can be used according to the invention can contain epitopes for at least 2, 3, 4, 5, 6, 7, 8, 9, 10 or more different probes.

Epitopes characteristic of different probes can be incorporated into the standards according to the invention by using polypeptide sequences which are identical to different regions of the A-beta peptide, and/or have at least a 50% homology thereto, but have the activity of the corresponding epitope.

In one embodiment, polypeptide sequences are used for this which identical or have a 50% homology with the N-terminal region of the A-beta polypeptide, and also polypeptide sequences which identical or have at least a 50% homology with the C terminus of the A-beta polypeptide.

In one embodiment of the present invention, the standard molecules contain so-called spacers.

A spacer is to be understood as meaning a molecule which is incorporated into the standard molecule via covalent bonds, and has certain physical and/or chemical properties, through which the properties of the standard molecule are altered. In one embodiment of the standards according to the invention, hydrophilic or hydrophobic, preferably hydrophilic, spacers are used. Hydrophilic spacers are selected from the group of the molecules formed from polyethylene glycol, sugar, glycerol, poly-L-lysine or beta-alanine.

In one alternative of the present invention, the standards that can be used according to the invention comprise (further) functional groups.

Functional groups are to be understood as meaning molecules which are covalently bonded to the standard molecules. In one variant, the functional groups contain biotin groups. This facilitates a strong covalent bond to streptavidin. Standard molecules containing biotin groups can thus be bonded to molecules containing streptavidin groups. If the standard molecules that can be used according to the invention contain biotin and/or streptavidin groups, then larger standards can thus be assembled, or a plurality of possibly different standard molecules can be bonded onto one backbone.

In a further alternative of the present invention, the standard molecules contain dyes for the spectrophotometric determination and/or aromatic amino acids. Aromatic amino acids are e.g. tryptophans, tyrosine, phenylalanine or histidine, or selected from this group. The incorporation of tryptophan facilitates a spectrophotometric determination of the concentration of standards in solution.

The present invention further provides the use of polypeptides containing dendrimers which, as regards their sequence, are identical in the corresponding part region with the endogenous proteins or have a homology of at least 50% over the corresponding part region with the endogenous proteins which characterize a protein aggregation disease.

The dendrimers can contain any of the above-described features of the standards or any desired combination thereof.

In one alternative of the present invention, they are dendrimers containing a precisely defined number of epitopes for the covalent bonding of probes has, dendrimer containing epitopes of the A-beta peptide.

To examine blood, blood products and/or organs for amyloid-beta oligomers, a standard can be used for quantifying pathogenic aggregates or oligomers of endogenous proteins which characterize a protein aggregation disease or an amyloid degeneration or protein misfolding disease, characterized in that a polymer is constructed from polypeptide sequences which, as regards their sequence, are identical in the corresponding part region with the endogenous proteins or have a homology of at least 50% over the corresponding part region with those endogenous proteins which characterize a protein aggregation disease or an amyloid degeneration or protein misfolding disease where the polymers do not aggregate.

For the binding of probes, the standard can have a precisely defined number of epitopes which are covalently linked together.

The standard can also contain epitopes of the A-beta peptide and/or the sequences according to the invention.

To examine blood, blood products and/or organs for amyloid-beta oligomers, the following method can also be used for the selective quantification of A-beta aggregates:
Method comprising the immobilization of A-beta capture molecules on a substrate, application of the sample to be examined onto the substrate, addition of probes characterized for the detection which label these as a result of specific binding to A-beta aggregates, and detection of the labeled aggregates.

This method for the selective quantification and/or characterization of A-beta aggregates comprises the following steps:
a) application of the sample to be examined onto the substrate,
b) addition of probes characterized for the detection which label these as a result of specific binding to A-beta aggregates and
c) detection of the labeled aggregates, where
step b) can be carried out before step a).

Standards are also provided which facilitate an exact and quantitative determination of pathogenic aggregates or oligomers of endogenous proteins. The standards should be able to be used as internal or external standards.

Furthermore, precisely defined, homogeneous and stable preparations of standards can be used for quantifying pathogenic aggregates or oligomers of endogenous proteins.

Standards for quantifying oligomers or pathogenic aggregates which characterize a protein aggregation disease or an amyloid degeneration or protein misfolding disease are characterized in that a polymer is constructed of polypeptide sequences which, as regards their sequence, are identical in the corresponding part region with the endogenous proteins, or have a homology of at least 50% over the corresponding part region with the endogenous proteins which characterize a protein aggregation disease or an amyloid degeneration or protein misfolding disease, where the polymers do not aggregate.

The standard can be characterized in that it has a precisely defined number of epitopes which are covalently linked together for the binding of probes.

The standard can also be characterized in that it contains epitopes of the A-beta peptide and/or the sequences according to the invention.

The standards are used as capture molecules according to the invention. In an alternative, the standards are used for the removal and/or detoxification of amyloid-beta oligomers in blood, blood products and/or organs.

In another embodiment, the present invention relates to a kit which comprises standard according to the invention and/or sequences. The compounds and/or components of the kit of the present invention can be packaged in containers, possibly with/in buffers and/or solution. Alternatively, some components can be packaged in the same container. Additionally to this or alternatively to this, one or more of the components could be absorbed onto a fixed support, such as e.g. a glass plate, a chip or a nylon membrane or onto the indentation of a microtiter plate. Furthermore, the kit can contain instructions for using the kit for any one of the embodiments.

The present invention also provides a kit for the selective quantification of A-beta aggregates according to the method described above. Such a kit can contain one or more of the following components:
substrate made of glass which is coated with a hydrophobic material;
standard;
capture molecule;
probe;
substrate with capture molecule;
solutions;
buffer.

The compounds and/or components of the kit of the present invention can be packaged in containers optionally with/in buffers and/or solution. Alternatively, some components can be packaged in the same container. Additionally to this or alternatively to this, one or more of the components could be absorbed on a fixed support, such as e.g. a glass plate, a chip or a nylon membrane or onto the indentation of a microtiter plate. Furthermore, the kit can contain instructions for using the kit for any of the embodiments.

In a further variant of the kit, the above-described capture molecules are immobilized on the substrate. Additionally, the KIT can contain solutions and/or buffer. To protect the dextran surface and/or the capture molecules immobilized thereon, these can be coated with a solution or a buffer.

The kit can also contain at least one standard or at least one dendrimer for the quantification of pathogenic aggregates or oligomers of endogenous proteins which contain a protein aggregation disease.

Polymers, D-peptides, antibodies, and/or compounds which can be used according to the invention in a method for treating (in vitro) blood, blood products and/or organs for removing and/or detoxifying amyloid-beta oligomers are shown below:

DB 4:
(SEQ ID NO: 1)
rprtrlrthqnr

D3D3:
(SEQ ID NO: 13)
rprtrlhthrnrrprtrlhthrnr

D3nwnD3:
(SEQ ID NO: 14)
rprtrlhthrnrnwnrprtrlhthrnr double-D3-free-Ntermini:
(SEQ ID NO: 15)
(rprtrlhthrnr)₂-PEG3 double-D3-free-Ctermini:
(SEQ ID NO: 16)
PEG5-(rprtrlhthrnr)₂

(SEQ ID NO: 2)
kqhhveygsdhrfead (SEQ ID NO: 3)
shyrhisp (SEQ ID NO: 4)
giswqqshhlva (SEQ ID NO: 5)
prtrlhth (SEQ ID NO: 6)
qshyrhispaqv (SEQ ID NO: 7)
qshyrhispdqv (SEQ ID NO: 8)
qshyrhispar (SEQ ID NO: 9)
kshyrhispakv (SEQ ID NO: 10)
rprtrlhthrnr (SEQ ID NO: 11)
rprtrlhthrte (SEQ ID NO: 12)
kprtrlhthrnr (SEQ ID NO: 17)
daefrhdsgye (SEQ ID NO: 18)
hhghspnvsqvr (SEQ ID NO: 19)
gsfstqvgslhr (SEQ ID NO: 20)
htgtqsyvprl (SEQ ID NO: 21)
tlayaraymvap (SEQ ID NO: 22)
tlayaraymvap (SEQ ID NO: 23)
atpqndlktfph (SEQ ID NO: 24)
tqpetdllrvqf (SEQ ID NO: 25)
citwpptglty (SEQ ID NO: 26)
tfletgpiyadg (SEQ ID NO: 27)
lvppthrhwpvt (SEQ ID NO: 28)
appgnwrnylmp (SEQ ID NO: 29)
dnysnyvpgtkp (SEQ ID NO: 30)
svsvgmkpsprp (SEQ ID NO: 31)
slpnpfsyssfg (SEQ ID NO: 32)
yvhnpyhlpnpp (SEQ ID NO: 33)
crrlhtyigpvt (SEQ ID NO: 34)
gatmkkmddhtv (SEQ ID NO: 35)
lgktqklsdahs (SEQ ID NO: 36)
ddqarpymaygp (SEQ ID NO: 37)
gdtwvnmvsmvh (SEQ ID NO: 38)
gytwvnmvsmvh (SEQ ID NO: 39)
wtntvarlatpy (SEQ ID NO: 40)
qtqalyhsrqvh (SEQ ID NO: 41)
nsqtqtlhlfph (SEQ ID NO: 42)
hntsanilhssh (SEQ ID NO: 43)
shinptsfwpap (SEQ ID NO: 44)
tfsnplymwprp (SEQ ID NO: 45)
gpspfnpqptpv (SEQ ID NO: 46)
fsdhksptpppr (SEQ ID NO: 47)
stsvyppppsaw (SEQ ID NO: 48)
yglptqansmql (SEQ ID NO: 49)
hnrtdntyirpt (SEQ ID NO: 50)
lqqplgnnrpns (SEQ ID NO: 51)
kpedsaaypqnr (SEQ ID NO: 52)
rpedsvitktqnt (SEQ ID NO: 53)
raadsgctptkh (SEQ ID NO: 54)
rprtrlhthrnt (SEQ ID NO: 55)
rprtrlhthtnv rprtrlhthtnr (SEQ ID NO: 56)

rprtrlhthrkq (SEQ ID NO: 57)

rprtrlhtlrnr (SEQ ID NO: 58)

rrrsplhthrnr (SEQ ID NO: 59)

lrsprqrripri (SEQ ID NO: 60)

rkrqlrmttprp (SEQ ID NO: 61)

shyrhispaqk (SEQ ID NO: 62)

double-D3-free-Ntermini:
(rprtrlhthrnr)2- (SEQ ID NO: 63)

double-D3-free-Ctermini:
(rprtrlhthrnr)2 (SEQ ID NO: 64)

DB 3:
rpitrlrthqnr, (SEQ ID NO: 65)

RD 2:
ptlhthnrrrrr (SEQ ID NO: 66)

RD 1:
pnhhrrrrrrtl (SEQ ID NO: 67)

RD 3:
rrptlrhthnrr (SEQ ID NO: 68)

D3-delta-hth:
rprtrlrnr (SEQ ID NO: 69)

NT-D3:
rprtrl (SEQ ID NO: 70)

DB 1:
rpitrlhtnrnr, (SEQ ID NO: 71)

DB 2:
rpittlqthqnr, (SEQ ID NO: 72)

D3:
rprtrlhthrnr (SEQ ID NO: 73 ())

DB 5:
rpitrlqtheqr (SEQ ID NO. 74)

D3-delta-hth D3-delta-hth:
rprtrlrnrrprtrlrnr (SEQ ID NO: 75)

RD 2-RD 2:
ptlhthnrrrrrptlhthnrrrrr (SEQ ID NO: 76)

DO 3:
sgwhynwqywwk (SEQ ID NO: 77)

rprtrsgwhynwqywwkrnr (SEQ ID NO: 78)

ptlsgwhynwqywwkrrrrr (SEQ ID NO: 79)

Antibodies which can be used according to the invention in a method for treating (in vitro) blood, blood products and/or organs for removing and/or detoxifying amyloid-beta oligomers are defined as follows:
antibodies which
a) bind to a retro-inverse sequence of the amyloid beta-peptide or amyloid beta-peptide part fragments and/or
b) bind to the multimerization domain of the amyloid beta-peptide and also to the amyloid beta-peptide and/or
c) bind to one of the aforementioned sequences according to the invention selected from the group:
SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 or homologous sequences thereof.

Hybrid compounds which can be used according to the invention in a method for treating (in vitro) blood, blood products and/or organs for the removal and/or detoxification of amyloid-beta oligomers are defined as follows:

Hybrid compound of the formula A-B, where A is an aminopyrazole or a derivative thereof, and B is a peptide and A and B are covalently joined together directly or by means of a linker.

Hybrid compound, characterized in that B is a D-peptide, characterized in that the D-peptide is selected from the aforementioned sequences according to the invention.

Hybrid compound of the formula A-B, characterized in that
A is selected from the group of the compounds consisting of: 3-aminopyrazole-5-carboxylic acid, derivatives thereof with replaced heterocyclic CH group for —CR— or —N—, —O—, —S—, 3-aminopyrazole-5-carboxylic acid dimer and also trimer or tetramer.
B is selected from the group of the compounds consisting of: D3-peptide, SEQ ID NO:1, SEQ ID N0:2, SEQ ID N0:3, SEQ ID N0:4, SEQ ID N0:5, SEQ ID N0:6, SEQ ID N0:7, SEQ ID N0:8, SEQ ID N0:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID N0:22, SEQ ID N0:23, SEQ ID N0:24, SEQ ID N0:25, SEQ ID N0:26, SEQ ID N0:27, SEQ ID N0:28, SEQ ID N0:29, SEQ ID NO:30, SEQ ID NO:31, SEQ ID N0:32, SEQ ID N0:33, SEQ ID N0:34, SEQ ID N0:35, SEQ ID N0:36, SEQ ID N0:37, SEQ ID N0:38, SEQ ID N0:39, SEQ ID NO:40, SEQ ID NO:41, SEQ ID N0:42, SEQ ID N0:43, SEQ ID N0:44, SEQ ID N0:45, SEQ ID N0:46, SEQ ID N0:47, SEQ ID N0:48, SEQ ID N0:49, SEQ ID NO:50, SEQ ID NO:51, SEQ ID N0:52, SEQ ID N0:53, SEQ ID N0:54, SEQ ID N0:55, SEQ ID N0:56, SEQ ID N0:57, SEQ ID N0:58, SEQ ID N0:59, SEQ ID NO:60, SEQ ID NO:61, SEQ ID N0:62, SEQ ID N0:63, SEQ ID N0:64. SEQ ID N0:65, SEQ ID N0:66, SEQ ID N0:67, SEQ ID N0:68, SEQ ID N0:69, SEQ ID NO:70, SEQ ID NO:71, SEQ ID N0:72, SEQ ID N0:73, SEQ ID N0:74, SEQ ID N0:75, SEQ ID N0:76, SEQ ID N0:77, SEQ ID N0:78 and SEQ ID N0:79;

the linker is selected from the group of the compounds consisting of:

no linker, GABA, TEG, TEG dimer, PEG, alpha-amino acids, alpha-amino-omega-carboxylic acid.

By means of the method according to the invention, pathogenic particles, amyloid-beta oligomers are removed and/or detoxified, i.e. converted to a nonharmful form or destroyed. Consequently, a further infection as a result of pathogenic (amyloidogenic) particles remaining and replicating is avoided. Here, synergistic effects arise, triggered by the compounds to be used according to the invention. Thus, in particular the co-aggregates of amyloid-beta peptides (oligomers) and the compounds to be used according to the invention lead, as a nonharmful form, to a subsequent prevention or reduction of further, or the new formation of, A-beta aggregates.

The method according to the invention is thus safer than the methods known from the prior art since it is not necessary for an absolutely remainder-free removal of the pathogenic, toxic and/or infectious particles to take place. A detoxification as a result of conversion to nonharmful forms takes place, which can even prevent or reduce a subsequent infection, i.e. the formation of A-beta aggregates.

BRIEF DESCRIPTION OF THE DRAWINGS

In the accompanying drawings.

DETAILED DESCRIPTION OF THE PRESENT INVENTION

Examples

1. ThT Seeding Assay: Principles

Figure 1:
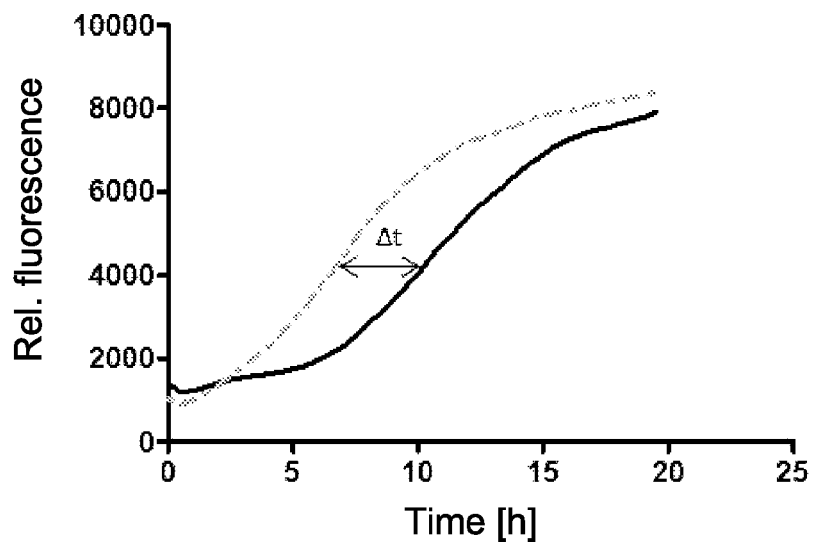
FIG. 1 is a diagram showing the relative fluorescence as a function of time in the experiment described below in the absence and presence of preformed Abeta aggregates which have formed without addition of inhibitor substances.

Amyloidogenic peptides have the ability to form amyloid fibrils. This can occur spontaneously with a certain probability. If no amyloid "germs" are present, it may take some time until the first amyloid fibrils are formed, the formation and replication of which can be quantitatively monitored with the help of the fluorescence from Thioflavin T (ThT). ThT interacts with A-beta fibrils and the fibril-dye complex exhibits increased fluorescence ($\lambda$em: 450 nm, $\lambda$ex: 490 nm). The time until the ThT signal begins to increase is called the "lag phase". This "lag phase" can be avoided or greatly shortened if amyloid "germs", also called "seeds", are added to the aggregation batch. A known example is the addition of prion-containing brain material to a solution of monomeric recombinant prion protein, which then forms ThT-positive fibrils with a significantly shortened "lag phase". A further example consists in the addition of a small amount of Abeta-amyloid fibrils to a solution of nonaggregated A-beta peptide (Abeta). Here too, the "lag phase" to the formation of ThT-positive Abeta fibrils is significantly shortened. Consequently, this test (called "ThT seeding assay") allows any desired substances or substance mixtures to be examined as to their content of germ-able amyloids. If the substance mixture added to the aggregation batch contains "seed"-able amyloids, this results in the lack or shortening of the "lag phase". This in vitro property is often considered analogously to the prion-like infectiosity or transmissibility in vivo.

In the first control experiment it was investigated whether preformed Abeta aggregates, being aggregation germs, actually shorten the "lag phase" of the aggregation of freshly dissolved Abeta. For this purpose, the ThT fluorescence of freshly dissolved Abeta was monitored in the absence and presence of preformed Abeta aggregates. Then, Abeta aggregates were prepared which were formed from a mixture of Abeta(1-42) and an inhibitor substance (in this example in each case one of the D-peptides D3, DB1, DB2, DB3, DB4, DB5), which should interfere in the formation of amyloid fibrils. The Abeta-inhibitor coaggregates formed in this way were added just like the amyloid Abeta aggregates to a ThT seeding assay in order to determine the remaining amyloid potential of these coaggregates.

2. ThT Seeding Assay: Experimental Details $\mu$M of A-beta peptide (1-42) were preincubated together with one of the inhibitor substances (20 $\mu$M) for 7 days at 37° C. in 10 mM NaPi pH 7.4. The sample was then centrifuged (20 min, 16 100×g), the aggregate pellet was washed 3× and resuspended in 10 mM NaPi pH 7.4. In an analogous manner, A$\beta$ fibrils were produced without inhibitor as positive control. Directly before the actual ThT seeding assay, fresh Aβ (20 µM in 10 mM NaPi pH 7.4) was mixed (80:20 volume fractions) with the resuspended aggregation germs which had formed in the presence or absence of the inhibitor substances, and 10 µM ThT were added thereto. The reference used was fresh A6 solution which was mixed with buffer solution without aggregation germs (80:20 volume fractions) and comprised 10 µM ThT. 50 µl of the respective reaction solution were pipetted into an indentation of a black 384-well microtiter plate. The ThT fluorescence was measured every 30 min over 20 h at an excitation wavelength of 440 nm and an emission wavelength of 490 nm. For the evaluation, the fluorescence intensity was corrected by subtraction of the 20% added aggregation germs and the average value was calculated. An eight-fold determination was carried out.

3. Procedure

FIG. 1 shows the course over time of the ThT fluorescence in the absence (solid line) and presence of preformed Abeta aggregates which have formed without the addition of inhibitor substances.

It can be clearly seen that these aggregates significantly increase the rate of the aggregation of fresh Abeta (Δt of about 4 h), i.e. clearly exhibit a seeding effect.

Figure 2:
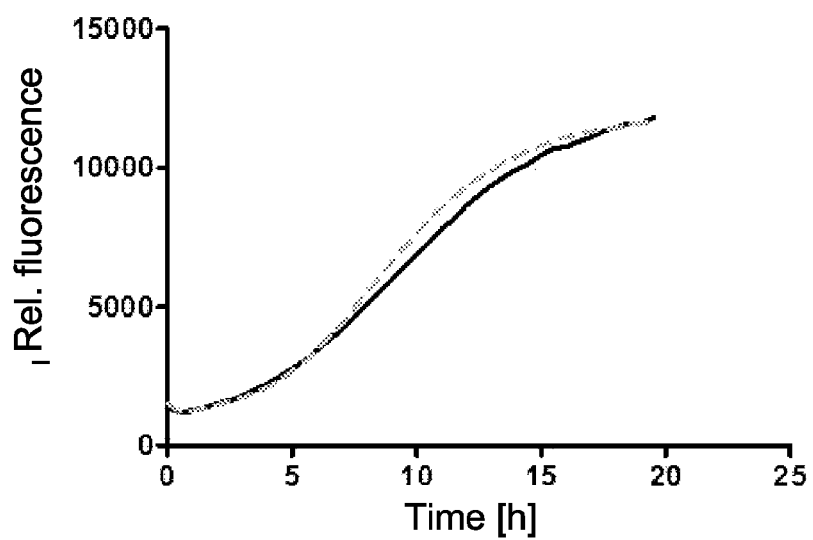
FIG. 2 is a diagram showing the relative fluorescence as a function of time in the experiment described below in the absence and presence of preformed Abeta aggregates which have formed before the start of the experiment with the addition of a first inhibitor substance.

FIG. 2 shows the course over time of the ThT fluorescence in the absence (solid line) and presence of preformed Abeta aggregates which have formed before the start of the experiment with the addition of the inhibitor substance D3.

It can be clearly seen that these aggregates are not able to increase the rate of the aggregation of fresh Abeta, i.e. clearly show no seeding effect.

Figure 3:
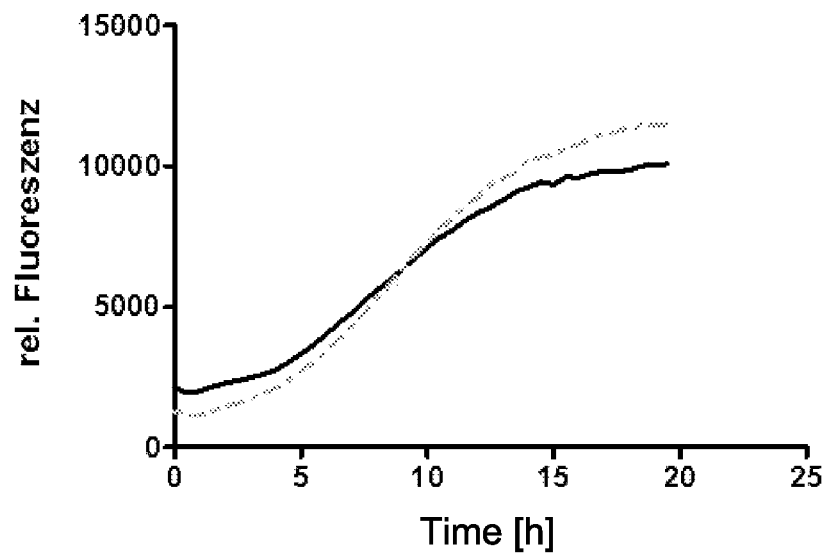
FIG. 3 is a diagram showing the relative fluorescence as a function of time in the experiment described below in the absence and presence of preformed Abeta aggregates which have formed before the start of the experiment with the addition of a second inhibitor substance.

FIG. 3 shows the course over time of the ThT fluorescence in the absence (solid line) and presence of preformed Abeta aggregates which have formed before the start of the experiment with the addition of the inhibitor substance DB1.

It can be clearly seen that these aggregates are not able to increase the rate of the aggregation of fresh Abeta, i.e. clearly exhibit no seeding effect.

Figure 4:
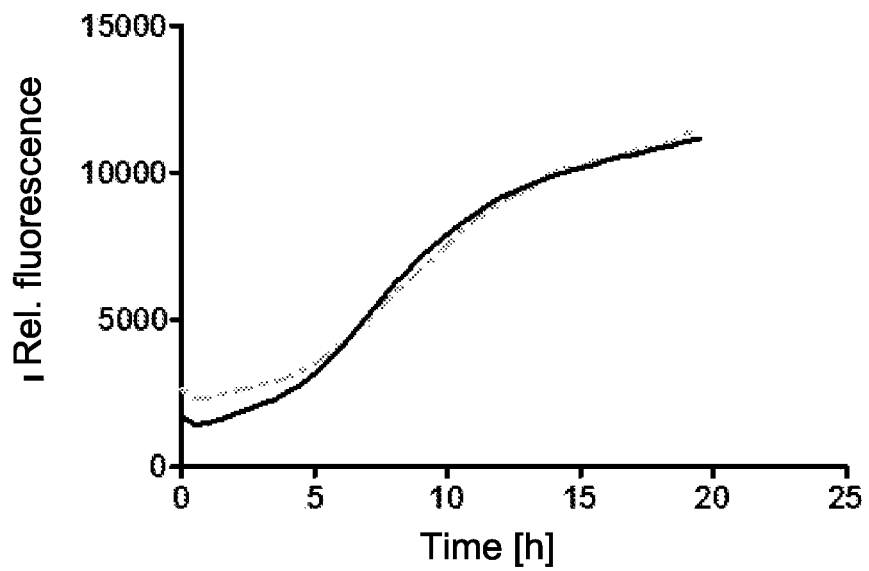
FIG. 4 is a diagram showing the relative fluorescence as a function of time in the experiment described below in the absence and presence of preformed Abeta aggregates which have formed before the start of the experiment with the addition of a third inhibitor substance.

FIG. 4 shows the course over time of the ThT fluorescence in the absence (solid line) and presence of preformed Abeta aggregates which have formed before the start of the experiment with the addition of the inhibitor substance DB2.

It can clearly be seen that these aggregates are not able to increase the rate of the aggregation of fresh Abeta, i.e. clearly exhibit no seeding effect.

Figure 5:
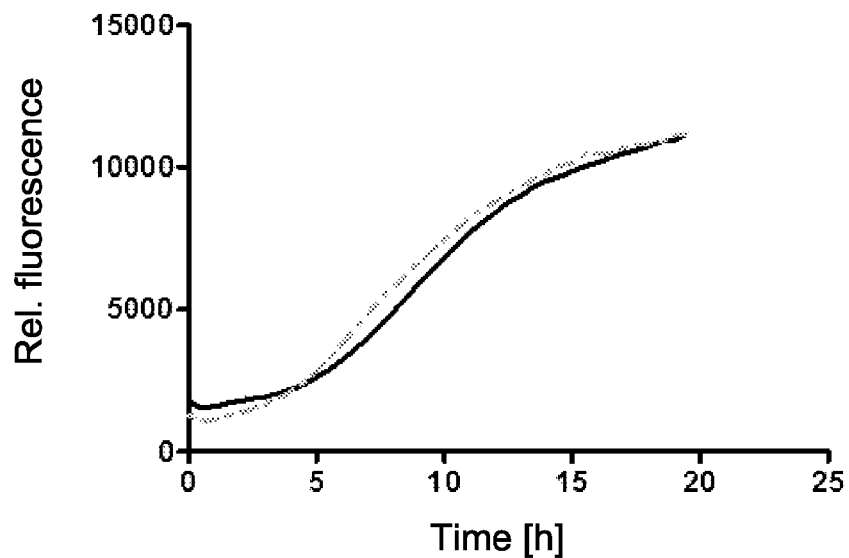
FIG. 5 is a diagram showing the relative fluorescence as a function of time in the experiment described below in the absence and presence of preformed Abeta aggregates which have formed before the start of the experiment with the addition of a fourth inhibitor substance.

FIG. 5 shows the course over time of the ThT fluorescence in the absence (solid line) and presence of preformed Abeta aggregates which have formed before the start of the experiment with the addition of the inhibitor substance DB3.

It can clearly be seen that these aggregates are not able to increase the rate of the aggregation of fresh Abeta, i.e. clearly exhibit no seeding effect.

Figure 6:
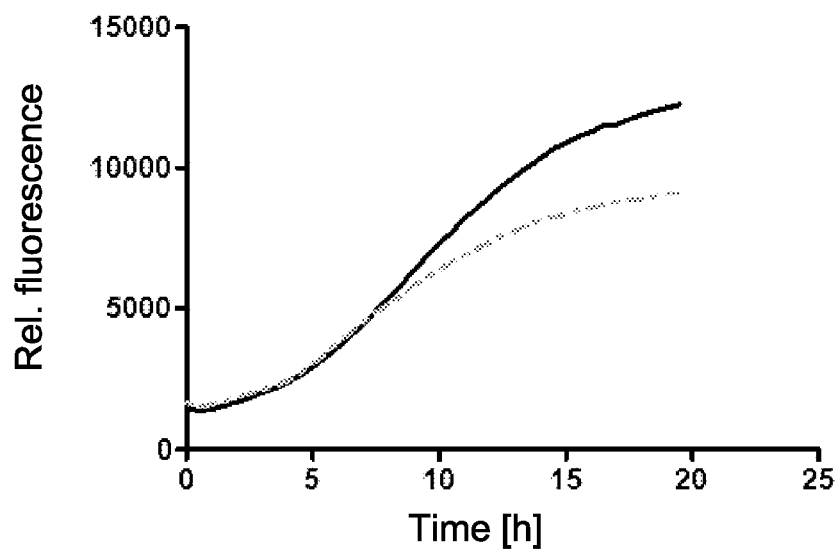
FIG. 6 is a diagram showing the relative fluorescence as a function of time in the experiment described below in the absence and presence of preformed Abeta aggregates which have formed before the start of the experiment with the addition of a fifth inhibitor substance.

FIG. 6 shows the course over time of the ThT fluorescence in the absence (solid line) and presence of preformed Abeta aggregates which have formed before the start of the experiment with the addition of the inhibitor substance DB4.

It can clearly be seen that these aggregates are not able to increase the rate of the aggregation of fresh Abeta, i.e. clearly exhibit no seeding effect. Moreover, the DB4-Abeta coaggregates even appear to reduce the formation of ThT-positive Abeta aggregates in the later phase.

Figure 7:
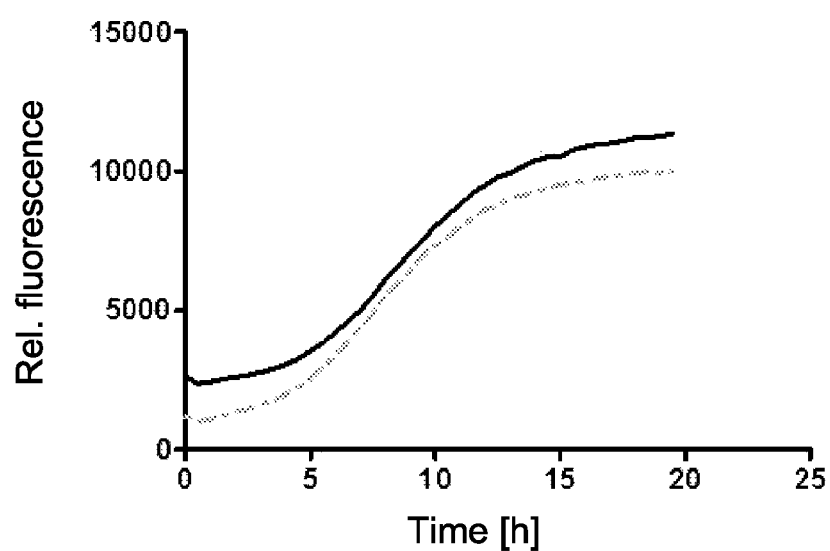
FIG. 7 is a diagram showing the relative fluorescence as a function of time in the experiment described below in the absence and presence of preformed Abeta aggregates which have formed before the start of the experiment with the addition of a sixth inhibitor substance.

FIG. 7 shows the course over time of the ThT fluorescence in the absence (solid line) and presence of preformed Abeta aggregates which have formed before the start of the experiment with the addition of the inhibitor substance DB5.

It can be seen that these aggregates are not able to increase the rate of the aggregation of fresh Abeta, i.e. clearly exhibit no seeding effect.

4. Summary of the Results

All of the tested D-peptides formed aggregates with Abeta which were no longer able to shorten the "lag phase" of the aggregation of freshly dissolved Abeta. These coaggregates are thus not amyloidogenic.

What is claimed is:

1. A method for treating blood, a blood product and/or an organ in vitro or ex vivo, wherein the method comprises removing the blood, blood product and/or organ from the human or animal body and removing and/or detoxifying amyloid-beta oligomers from the removed blood, blood product and/or organ, and wherein the method comprises contacting the blood, blood product and/or organ with one or more compounds which comprise the compound rprtrlrthqnr (DB 4:SEQ ID NO:1).

2. The method of claim 1, wherein the method further comprises examining the blood, blood product and/or organ for the presence of amyloid-beta oligomers prior to removing the blood, blood product and/or organ from the human or animal body.

3. The method of claim 1, wherein the one or more compounds are arranged as capture molecules on a support, via which a sample containing the blood, blood product and/or organ is passed.

4. The method of claim 3, wherein the capture molecules are fixed onto beads.

5. The method of claim 3, wherein the capture molecules are immobilized on nanomagnets.

6. The method of claim 3, wherein the capture molecules are arranged in a dialysis system.

7. The method of claim 3, wherein the support for the capture molecules is made of a biocompatible material.

8. The method of claim 3, wherein the support for the capture molecules is selected from one or more of membranes, filters, filter sponges, beads, rods, cords, column, hollow fibers.

9. The method of claim 1, wherein a kit is used for a selective quantification of A-beta aggregates and/or for treating (in vitro) blood, a blood product and/or an organ, the kit comprising one or more of:

a substrate made of glass which is coated with a hydrophobic material;
a standard;
a capture molecule;
a probe;
a substrate with capture molecule;
one or more solutions;
a buffer.

10. The method of claim 1, wherein the one or more compounds are passed as capture molecules ex vivo over and/or through an organ.

11. The method of claim 1, wherein the method comprises removing amyloid-beta oligomers from blood, a blood product and/or an organ.

12. The method of claim 11, wherein Alzheimer's disease is treated.

13. The method of claim 1, wherein the method comprises detoxifying amyloid-beta oligomers present in blood, a blood product and/or an organ.

14. The method of claim 13, wherein Alzheimer's disease is treated.

15. The method of claim 1, wherein the one or more compounds further comprise one or more hybrid compounds of formula A-B, where A is an aminopyrazole or a derivative thereof, and B is a peptide selected from SEQ ID NO:1, SEQ ID NO:13, SEQ ID NO:14, SEQ ID NO:15, SEQ ID NO:16, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, and A and B are covalently bonded to one another directly or by a linker.

* * * * *